United States Patent [19]
Walters

[11] Patent Number: 5,792,085
[45] Date of Patent: Aug. 11, 1998

[54] PRESSURE APPLICATION UNIT FOR POSITIONING VERTEBRA

[76] Inventor: David J. Walters, P.O. Box 637, Erwin, Tenn. 37650

[21] Appl. No.: 661,822

[22] Filed: Jun. 11, 1996

[51] Int. Cl.[6] .............................. A61F 5/00; A61B 17/56; A61B 17/00
[52] U.S. Cl. .............................. 602/19; 606/54; 606/201
[58] Field of Search .............................. 602/67–73, 19; 606/201, 204, 54

[56] References Cited

U.S. PATENT DOCUMENTS

| | | | |
|---|---|---|---|
| 2,835,247 | 5/1958 | Stabhok | 602/19 |
| 5,007,412 | 4/1991 | DeWall | 602/19 |
| 5,571,076 | 11/1996 | Cooper | 602/19 |

FOREIGN PATENT DOCUMENTS 3819859  12/1989  Germany .............................. 606/204

Primary Examiner—Glenn K. Dawson

[57] ABSTRACT

A device for applying external pressure to one or more vertebra for repositioning the same and/or maintaining the position thereof in the spinal column, or for forcing and maintaining segments of a broken vertebra in healing contact with each other. The device has an upper body vest adapted to substantially surround the upper body of a patient in a snug manner whereby the vest is substantially immovable relative to the upper body. The vest has front and back sections provided with cooperating elements of an attachment mechanism such as Velcro or belt and adjustable buckle, for clamping the sections to the upper body. The back section has a pressure applicator unit extending substantially the length of the back section for applying external pressure, generally posteriorly to one or more vertebra. The applicator has a plunger such as a screw mounted for controlled, reciprocable movement in a direction toward the spine for applying the external pressure in a controlled manner to one or more vertebra areas.

9 Claims, 4 Drawing Sheets

5,792,085

PRESSURE APPLICATION UNIT FOR POSITIONING VERTEBRA

BACKGROUND OF THE INVENTION

1. Field of the Invention

This invention relates to a back treatment device and more particularly to a device which can apply force and pressure to selected portions of the human spine i.e., specific vertebra or segments thereof such as the spinous, mammillary, superior and inferior articular, and transverse processes, without effecting pressure-caused discomfort to other portions of the patients body.

2. Description of the Prior Art

Most individuals experience back problems at some point in their lives, either thru normal wear and tear or thru accident. These problems often are centered about displacement of one or more vertebra thru injury to spinal discs, or ligament damage, e.g., to the supraspinous, posterior longitudinal, ligamentum flavum, interspinal, or anterior longitudinal ligaments, or back muscle tear, or thru actual vertebra fracture whereby a segment of the vertebrae is in a fractured and dislocated condition. Various treatment mechanisms and methods are utilized to treat such back ailments or injuries and associated trauma and often include devices which strap to the patient for applying force and pressure to specific localized areas of the spine.

It is of course, often advantageous to apply such force to specific portions of the spine for lengthy rehabilitative periods and with varying degrees of pressure at different times during the healing period.

Many mechanisms have been developed for applying such pressures as indicated by U.S. Pat Nos. 5,086,757; 3,709,216; 5,507,135; 2,593,624; 1,424,884; 5,135,471; 2,180,775; 3,926,182; 2,835,247; 5,127,897, the disclosures of which with regard to utility, construction materials and specific structures or the like are hereby incorporated herein in their entirety.

In the use of these prior mechanisms very noticeable problems arise such as limited adjustability, if any, of the pressure point, particularly with respect to angular positioning about or in the plane of the spinal axis. Also, these mechanisms are typically very complex and employ straps or the like girding the body at spaced locations for generating the necessary opposing forces to the pressure applicator. Such straps cause discomfort to the patient, especially where the application of pressure is over a period of more than a few minutes and the pressure is of a significant degree.

OBJECTS OF THE INVENTION

Accordingly, it is a principal object of the present invention to provide a therapeutic pressure applicator device adapted to be worn by the patient and which is comfortable over long periods of time and which can apply any degree of pressure, in a wide range of axial and lateral selected angles, to selected vertebra areas of the spine.

The above and further objects hereinafter becoming evident have been attained in accordance with the present invention thru the discovery of structure for a pressure applicator device which, in its broad context, is defined as a device for applying external pressure to one or more vertebra for repositioning the same and/or maintaining the position thereof in the spinal column, and with respect to the spinal axis or for forcing and maintaining segments of a fractured vertebra in healing contact with each other, said device comprising an upper body vest means adapted to substantially surround the upper body of a patient in a snug manner whereby said vest means is substantially immovable relative to said upper body, said vest means having front and back sections provided with cooperating segments of attachment means for clamping said sections to said upper body, said back section having a spinal plane, pressure applicator means on said back section extending substantially the length of said back section for applying external pressure, generally posteriorly to one or more vertebra, said applicator means having thrust means mounted for controlled, reciprocable movement generally normal to said spinal axis for applying said external pressure in a controlled manner to one or more vertebra.

In certain preferred embodiments:

(a) said plunger means is mounted for limiting, universal type motion whereby pressure can be directed in a wide range of angles against the spine;

(b) said vest means comprises sections which are custom formed to fit a particular patients body; and (c) said cooperating elements of said attachment means comprises quick release hook and loop (Velcro) segments.

BRIEF DESCRIPTION OF THE DRAWINGS

The invention will be further understood from the following description and drawings of certain preferred embodiments wherein portions of the structure are shown enlarged for purposes of clarity and wherein the figures are not drawn to the same scale.

DETAILED DESCRIPTION OF THE DRAWINGS

Figure 1:
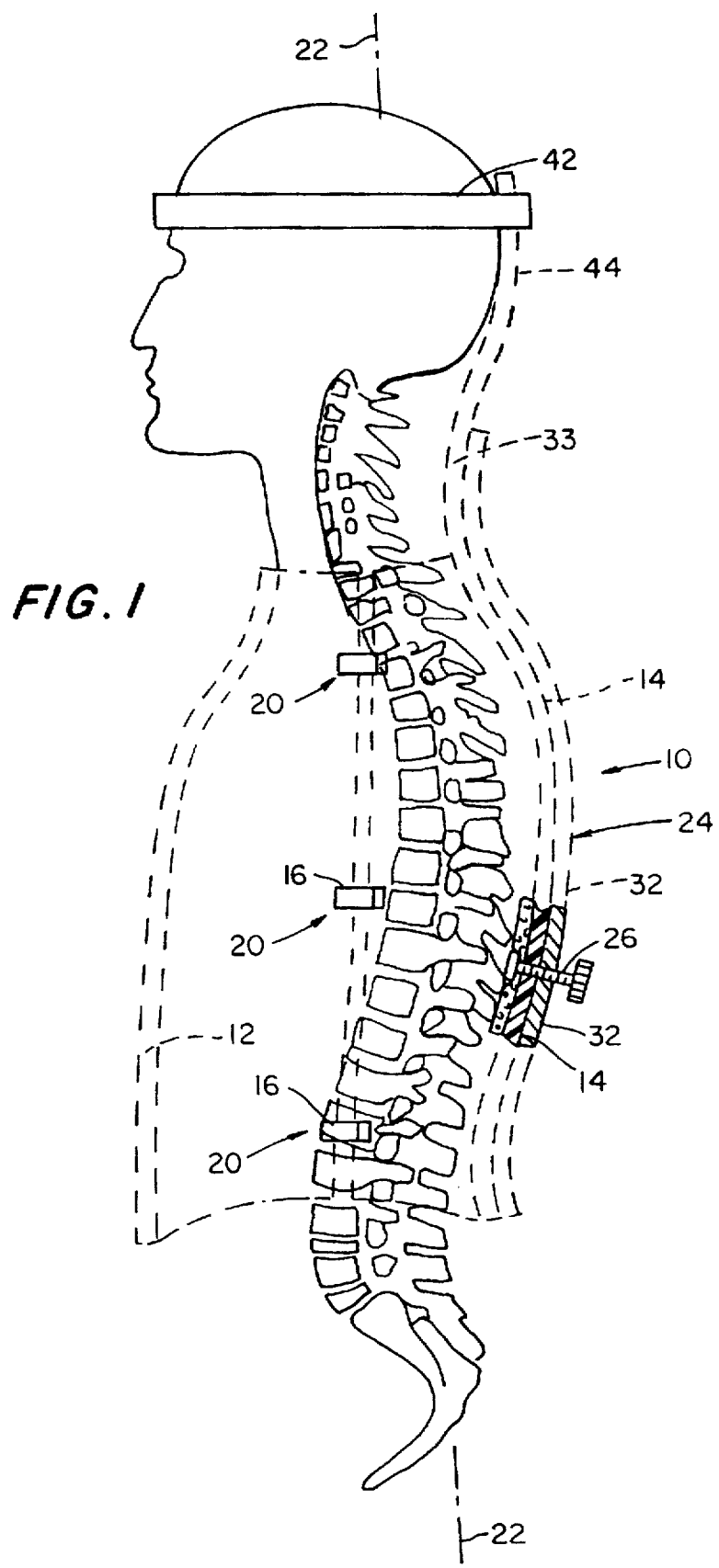
FIG. 1 is a side view of a patient wearing a simplified embodiment of the present device with portions thereof shown in phantom line.

The invention will be further understood from the following description with particular reference to the claims hereof, wherein the present device comprises an upper body vest means generally designated 10 dimensioned and adapted to substantially surround the upper body of a patient in a snug manner from approximately the waist to the head whereby said vest means is substantially immovable relative to said upper body, said vest means having front 12 and back 14 sections provided with cooperating segments 16, 18 of attachment means generally designated 20 for clamping said sections to said upper body, said back section 14 having an approximate spinal axis generally designated 22, pressure applicator means generally designated 24 on said back section extending substantially the length of said back section for applying external pressure, generally posteriorly to one or more vertebra 27 along the length of the spine 25, said applicator means having thrust means generally designated 26 mounted for controlled, reciprocable movement generally normal to said spinal axis for applying said external pressure in a controlled manner to one or more vertebra.

Each vest section may be comprised of any material which can afford both rigidity and comfort and preferably has a rigid or at least semi-rigid backing means 28 such as a vinyl, polyurethane, polyolefin, polyester, polyamide, plaster or paris, or the like, preferably in molded form. In this regard, the backing means may be form-fitted during its molding or forming to precisely fit a patients body contours for maximizing patient comfort and performance of the vest means.

In a most preferred embodiment, a cushion means 30 is adhered or otherwise affixed to the inside of the vest sections to allow the sections to be latched tightly to the body whereby the cushion means acts to distribute the reactive force to the pressure generated by the applicator means over large areas of the body, thus avoiding localized pressure points and their attendant discomfort. The cushion means preferably is of sponge type plastic material such as polyurethane or vinyl foam or the like, but also may be of thick, felt-like fabric or similar construction.

Figure 2:
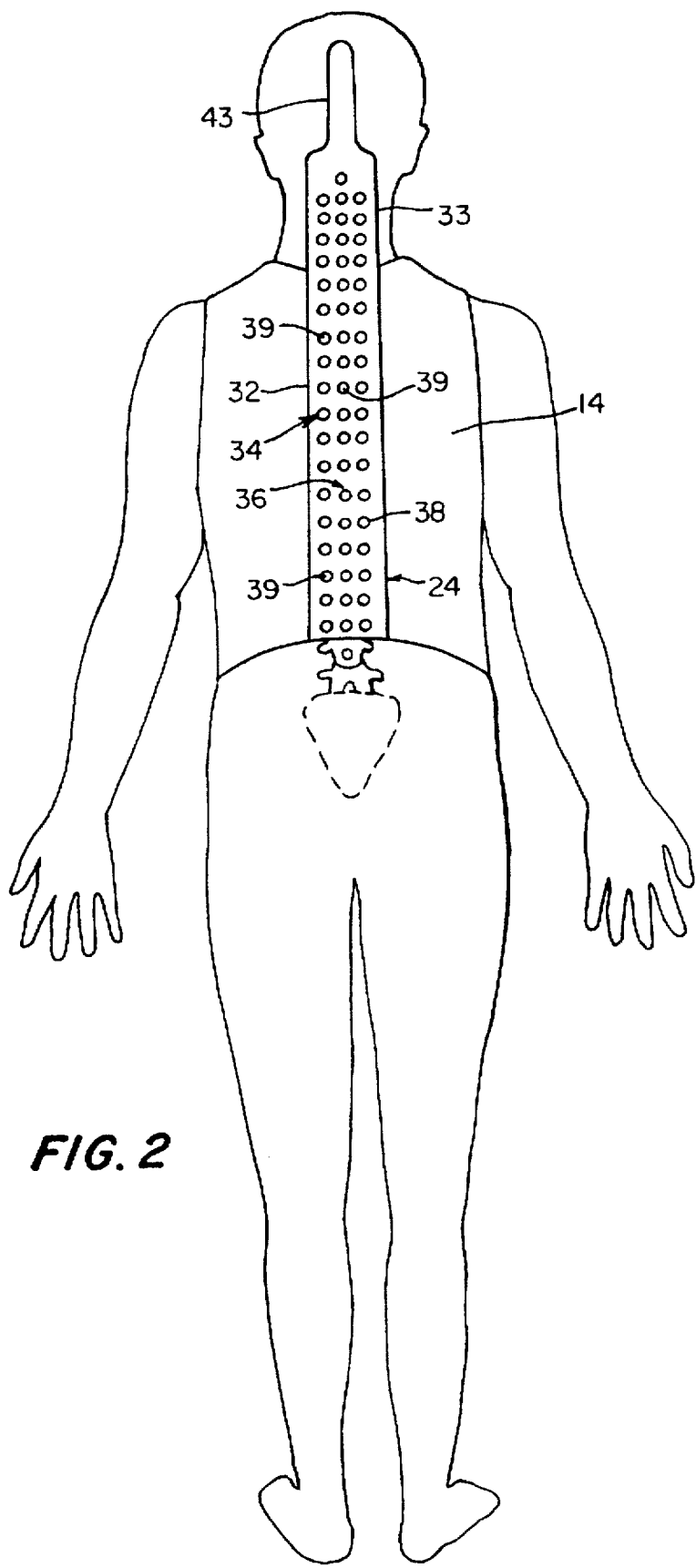
FIG. 2 is a rear view of the patient and device of FIG. 1.
Figure 3:
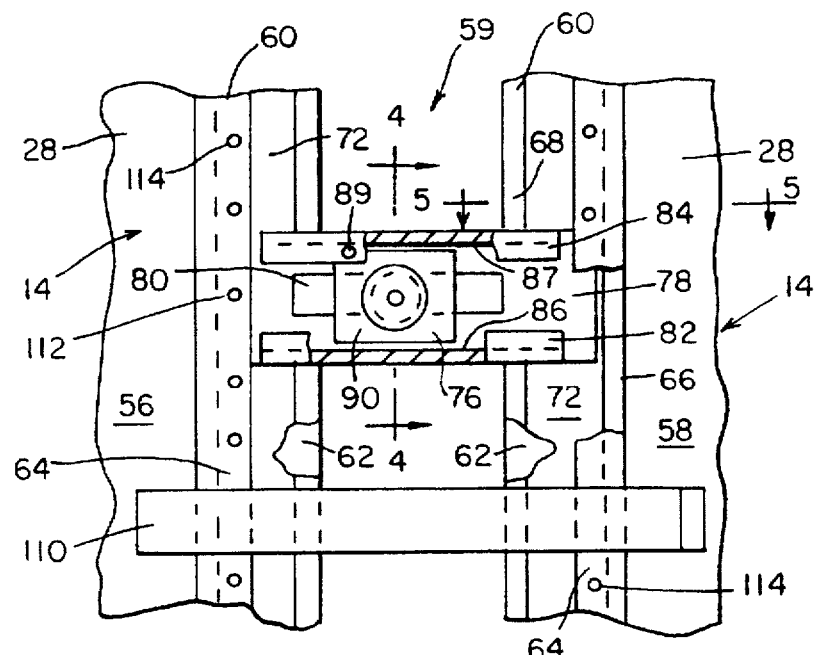
FIG. 3 is a rear elevational view of a preferred embodiment of the pressure applicator means with portions of the structure broken away for clarity.
Figure 4:
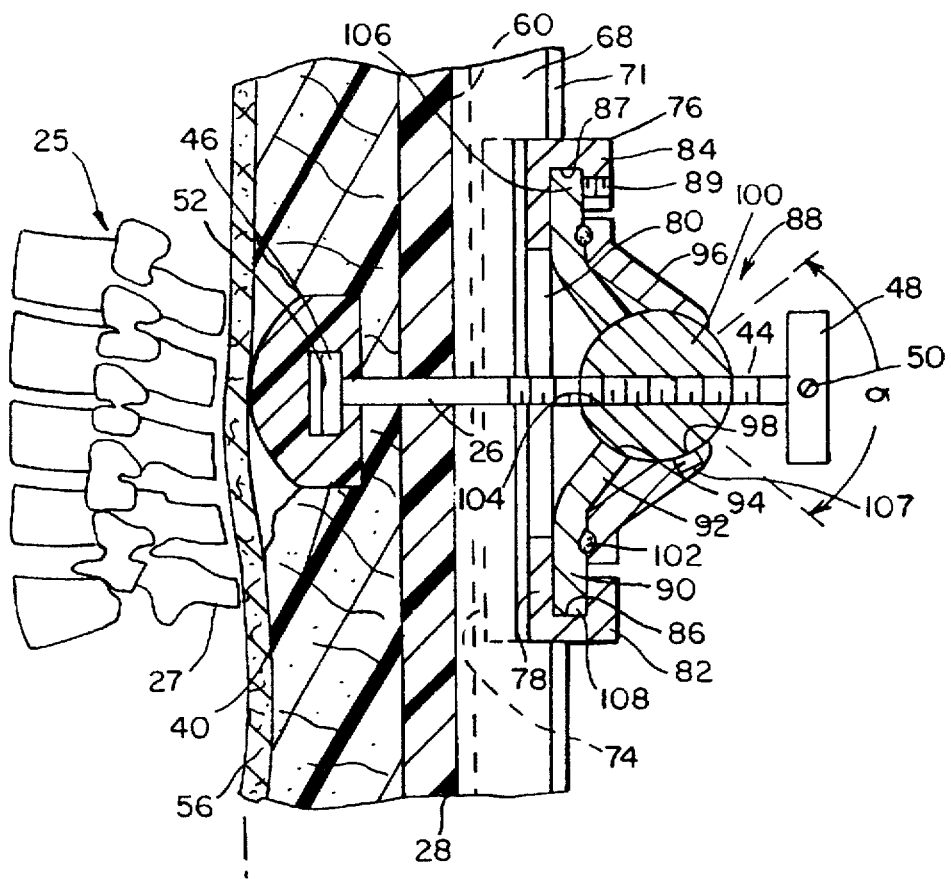
FIG. 4 is a cross-sectional view taken along line 4—4 of FIG. 3 in the direction of the arrows.
Figure 5:
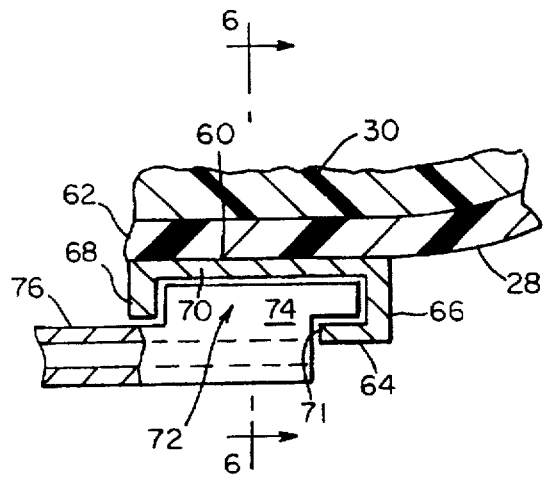
FIG. 5 is a cross-sectional view of one of the vertical rail means taken along line 5—5 of FIG. 3 in the direction of the arrows.
Figure 6:
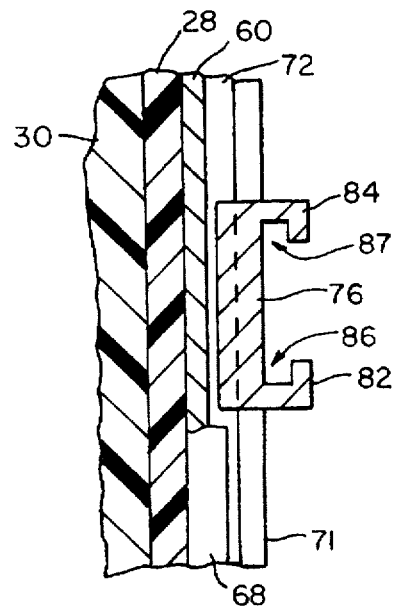
FIG. 6 is a cross-sectional view taken along line 6—6 of FIG. 5 in the direction of the arrows.

Referring to the embodiment of FIGS. 1 and 2, the pressure applicator means 24 preferably comprises an elongated thickened metal or plastic segment or portion 32 of back section 14 which is provided with one or more rows such as 34, 36, 38 of threaded apertures 39 in which the thrust means 26 is adapted to be threadedly mounted such that it can be screwed inwardly to force its crown 40 against the spine area. These apertures are axially and laterally positioned with respect to the vertebra, e.g., of an average height person, such that the thrust means can apply forces to selected vertebra. In this regard, the apertures of rows 34 and 38 may be slanted inwardly toward the spinal axis such that the pressure can be directed, e.g., toward the transverse process rather than straight on, as against the spinous process.

The segment 32 preferably extends upwardly as portion 33 to adjacent the base of the skull such that pressure can be applied to cervical vertebra as well. This portion 33 is preferably curved concavely such that apertures 39 of rows 34 and 38 are directed inwardly, e.g., toward the superior articular facets of the cervical vertebra. In the use of this portion 33, a head strap such as 42 affixed to an extension such as 44 of portion 33 may be employed to maintain the head against said extension and keep at least an approximate axial alignment of the cervical spine as pressure is applied thereto.

The attachment means 20 may be of any convenient construction including strap and button, belt and buckle, grommet and button type snap fastener, zipper, and preferably cooperating Velcro loop and pile elements.

Figure 7:
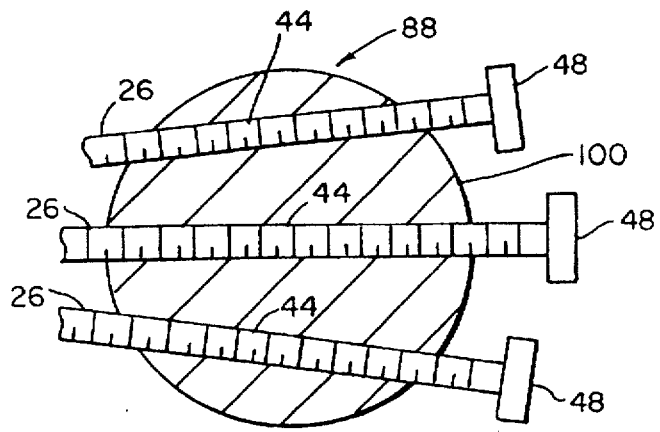
FIG. 7 is a view as in FIG. 4 of a variation of the plunger construction.

One preferred form of the thrust means 26 is shown in FIG. 7 and comprises a threaded shaft or screw 44 having a flanged inner end 46 and a handle means 48 preferably held onto the shaft by set screw 50 or equivalent structure. A rubber-like, fairly rigid crown 40 is provided rotatably on said inner end of the screw and is provided with a metal rub plate 52, preferably imbedded and non-rotatable in said crown and against which said inner end 46 can slide such that rotation of said shaft will not tend to rotate crown 40.

In the use of the embodiment of FIGS. 1, 2 and 7, a particular hole 39 location is selected for the thrust means and the shaft 44 thereof, with the handle 48 removed, is threaded thru the aperture to a point as shown in FIG. 7 where the semi-rigid crown 40 is forced into the softer cushion 30 and lies substantially in the plane 54 of the patients skin 56. The handle is then reattached to shaft 44. The vest sections are then latched together with sufficient force to snugly fit the patients body and thereby essentially fix the relative positions of the thrust means and the spinal portion against which pressure is to be exerted. The screw shaft 44 is then rotated to the desired extent to reposition the vertebra or a segment thereof.

It is particularly noted that two or more such thrust means can be employed at the same time such that, e.g., for a particular vertebra pressures can be applied not only to the area of the spinous process, but also to the area of either or both transverse processes, simultaneously.

Referring to the preferred embodiments of FIGS. 3–7, the back section 14 of the vest is provided as two halves 56 and 58, the halves being separated by a gap 59 and each half comprising the rigid or semi-rigid backing means 28 having the cushion means 30 affixed to the inside thereof and having a vertical rail means 60 affixed to its inner or spinal edge portion 62. Each rail means is formed with vertically extending wall sections 64, 66, 68 and 70 which provide a vertical slot generally designated 72. The term "vertical" as used throughout this application signifies the general posture attitude of the present device when worn by a patient in a standing position and is not intended to represent a mathematically precise orientation.

Slots 72 are dimensioned such that the end portions 74 of a slide plate generally designated 76 may be inserted therein, e.g., from the bottom of the rails 60, and the slide plate then slid upwardly to any desired vertical position between said rails. Said plate 76 is formed with a base 78 having a rectangular opening 80 therethrough and having wall segments 82 and 84 providing opposed grooves 86 and 87 respectively.

In this embodiment, the thrust means 26 has a universal type of mounting 88 which allows the thrust means e.g., screw, to be pivoted in practically any direction, i.e., laterally, vertically, or diagonally, of course to a limited degree such as thru the angle such that the crown 40 can bear on the exact spinal area selected by the therapist or doctor.

Mounting 88 as shown is a preferred example only of useful structure and comprises a plate-like slide support 90 having a first segment 92 formed with a circular aperture 94, and a second segment 96 formed with a circular aperture 98. A generally ball shaped member 100 of e.g., metal or plastic is pivotally mounted between said segments which are welded together as at 102 after the ball has been so placed. The thrust shaft 44 is threaded through a bore 104 in the member 100 for screw movement toward and away from the spine. A set screw 107 of the like may be used to lock the ball in a desired position. The upper 106 and lower 108 edges of support 90 are dimensioned to slide in groove 86 in slide pate 76 formed by edge portions 87 to allow lateral adjustment positioning of the plunger means. One or more set-screws 89 or the like threaded into either or both of wall segments 82 and 84 may be used to fix the laterally adjusted position of support 90 with respect to the spine. As shown in FIG. 7, a more sophisticated mounting 88 is shown wherein multiple screws can be mounted at any desired angles relative to each other in multiple threaded apertures in member 100 for providing simultaneous pressures to adjacent areas of the spine.

In using the mounting structure of FIGS. 3–7, the two halves of the back section 14 of the vest are securely held together in the area where pressure is to be applied, by the interlocking structure of the end portions 74 of slide plate 76 and wall sections 64, 66, 68 and 70 of the vertical rail means 60. In order to ensure that all portions of the vest are maintained in snug contact with the patients body, any number of releasable latching means such as Velcro straps 110 or belts and buckles or the like affixable to both halves of back section 14 may be used below and above the slide plate to pull the halves toward each other after said slide plate is properly positioned. The slide plate may be releasably locked in vertical adjusted position by one or more set screws 112 or the like selectively placed in threaded apertures 114 in wall sections 64 of the vertical rails.

The invention has been described in detail with particular reference to preferred embodiments thereof, but it will be understood that variations and modifications will be effected with the spirit and scope of the invention.

I claim:

1. A device for applying external pressure to one or more of a patients vertebra for repositioning the same and/or maintaining the position thereof in the patients spine, or for forcing and maintaining segments of a broken vertebra in healing contact with each other, said spine lying generally along a spinal axis, said device comprising an upper body vest means adapted to substantially surround the upper body of a patient from adjacent the waist to adjacent the neck in a snug manner, said vest means having front and back sections provided with cooperating segments of attachment means for clamping said sections to each other to snugly surround said upper body, said back section having an elongated, substantially rigid portion extending substantially the length of said back section and formed to closely conform to the curvature of the patients spine and lie adjacent thereto, a first element of a pressure applicator means provided on said elongated portion, thrust means providing a second element of said applicator means and being mounted on said first element for controlled, reciprocable movement relative to said first element in a direction generally normal to said spinal axis for applying external pressure in a controlled manner to a selected portion of said spine.

2. The device of claim 1 wherein mounting means is provided for said thrust means for allowing a universal movement of said thrust means whereby pressure can be directed in a wide range of angles against selected portions of the spine.

3. The device of claim 2 wherein said mounting means comprises a generally ball shaped member mounted in a socket shaped base affixed to said elongated portion wherein said thrust means is threadedly mounted thru said member and said member is pivotal within said base for adjusting the angle of said thrust means in a generally universal manner relative to the spine.

4. The device of claim 3 wherein said mounting means is provided on a slide support having upper and lower edge portions mounted on slide plate means for generally laterally directed adjustment motion with respect to said spinal axis, and wherein side edge portions of said slide plate means are mounted for vertical adjustment motion in vertical slots provided on said rail means operatively attached to said elongated portion, whereby the pressure applied by said thrust means can be directed in a wide range of angles to the spine at essentially any vertical location along the spine.

5. The device of claim 3 wherein multiple thrust means are mounted in said ball shaped member.

6. The device of claim 1 wherein said vest means is custom formed to fit snugly a particular patients body.

7. The device of claim 1 wherein said cooperating segments of said attachment means comprises quick release hook and loop segments.

8. The device of claim 1 wherein said pressure applicator means comprises at least one row of vertically spaced threaded apertures in which apertures one or more said thrust means can be selectively threaded.

9. The device of claim 1 wherein the inner surfaces of said vest means sections are provided with cushion means affixed thereto for cushioning the patient's upper body against reactive forces generated by pressure developed by operation of said pressure applicator means.

* * * * *